United States Patent [19]
Burt et al.

[11] Patent Number: 5,074,848
[45] Date of Patent: Dec. 24, 1991

[54] NEEDLE RECEPTACLE

[76] Inventors: Wayne R. Burt; William M. Burt, both of 2395 Bernadine Dr., Salt Lake City, Utah 84109

[21] Appl. No.: 556,621

[22] Filed: Jul. 23, 1990

Related U.S. Application Data

[63] Continuation-in-part of Ser. No. 203,298, Jun. 2, 1988, abandoned.

[51] Int. Cl.⁵ .............................................. A61M 5/00
[52] U.S. Cl. .................................. 604/263; 604/192; 604/197; 128/919; 206/365
[58] Field of Search ............... 604/187, 192, 197, 198, 604/263; 206/363–366, 571; 128/919

[56] References Cited

U.S. PATENT DOCUMENTS

| | | | |
|---|---|---|---|
| 4,659,330 | 4/1987 | Nelson et al. | 604/192 |
| 4,795,443 | 1/1989 | Permenter et al. | 604/198 |
| 4,840,272 | 6/1989 | Goldman | 206/365 |
| 4,883,470 | 11/1989 | Haindl | 604/192 |
| 4,906,235 | 3/1990 | Roberts | 604/192 |
| 4,946,447 | 8/1990 | Hardcastle et al. | 604/198 |
| 4,994,046 | 2/1991 | Wesson et al. | 604/198 |
| 5,002,536 | 3/1991 | Thompson et al. | 604/192 |

*Primary Examiner*—John D. Yasko
*Assistant Examiner*—Mark O. Polutta
*Attorney, Agent, or Firm*—M. Reid Russell

[57] ABSTRACT

A needle receptacle that includes a sheath with a cradle portion and attached barrel end and may include top and end covers as a syringe and needle housing. The cradle portion is open along its top portion and includes parallel spaced apart finger protective flanges at opposite sides of a finger grasping portion formed therearound. The barrel end is tapered into a needle receiving portion and includes a flared connection between the cradle and the barrel end to serve as a guide for needles inserted into the barrel, which barrel also includes a detent extending radially therein for preventing needle turning.

6 Claims, 2 Drawing Sheets

NEEDLE RECEPTACLE

PRIOR ART

The present application is a continuation-in-part application from a U.S. patent application, Ser. No. 07/203,298, filed June 2, 1988, that is abandoned with this filing.

BACKGROUND OF THE INVENTION

Field of the Invention

This invention relates to covers for hypodermic needles and is particularly concerned with covers that will prevent accidental needle stick injuries and transmission of infection to healthcare workers and others.

Among the covers proposed to reduce instances of needle stick injuries resulting from the return of a used needle to a cover are those shown in U.S. Pat. Nos. 2,571,654, 3,780,734, 4,425,120, 4,801,295 and 4,867,746, all of which are intended to slide downwardly over the used needle. U.S. Pat. Nos. 4,573,976 and 4,643,722 are directed to guards that move across the needle head end of a syringe to rest that needle in a groove or slot of the guard. Also, needle protectors that cap over a needle are shown in U.S. Pat. Nos. 3,381,813 and 4,659,330, and a cradle with a closed needle end stop is shown in U.S. Pat. No. 4,795,443. A similar device is shown in United Kingdom Patent No. 2,202,446A, and telescoping guards are shown in U.S. Pat. Nos. 4,804,372 and 4,840,272.

U.S. Pat. Nos. 4,559,042, 4,573,975 and 4,629,453 disclose covers having enlarged disks surrounding a needle receiving opening, with the disks intended to deflect errant needles and to protect the fingers of the user grasping the covers behind the disks.

U.S. Pat. Nos. 4,610,667 and 4,623,336 disclose covers having cylindrical needle receiving barrels with funnel shaped receiving ends. A funnel shaped end to direct a needle into the barrel so as to protect the fingers of a user grasping the barrel.

U.S. Pat. No. 4,654,034 discloses a cover that utilizes both a funnel shaped end on a cylindrical receiving barrel and a disk extending outwardly from the barrel as secondary protection for the fingers of a user grasping the barrel.

In using any of the covers disclosed in the previously identified patents, the cover is pulled or pushed onto the needle or the needle is pushed into the cover with that needle being moved toward the user's fingers or with the user's fingers moved towards the needle.

U.S. Pat. Nos. 3,658,061, 4,664,259 and 4,659,330 disclose covers that pivot off needles and then pivot back onto the needles after the needles have been used. These patents require the use of hinged body structures that are relatively expensive to construct and that have slots to permit the covers to pivot over the used needles. The slots remain unsealed, thus reducing the protection offered.

None of the cited patents involve the cradle syringe holder and ribbing therefore like that of the present invention.

SUMMARY OF THE INVENTION

Hypodermic needles, such as are generally used for the giving of injections or withdrawal of blood samples are commonly equipped with a disposable cap that protects the needle prior to use. Such caps are intended to provide protection for the needle against contamination and physical damage and are generally made replaceable to cover the needles after they have been used to prevent accidental needle sticks.

Accidental needle sticks occurs all too frequently, even though users are warned to be careful in reinserting needles into covers.

Because the dangers of transmission of diseases from needle sticks have long been recognized, and because it has been known that many diseases, including hepatitis, acquired immune deficiency syndrome (AIDS), and others can be transferred through needle sticks a great many proposals have been made for covers that will reduce the incidence of disease transmission.

OBJECTS OF THE INVENTION

Principal objects of the present invention are to provide a cradle type receptacle or cover that accommodates insertion of a hypodermic syringe having a needle extending from one end where the needle is pushed away from the body and grasping fingers of a user or operator and that will fully seal the used needle.

Other objects are to provide such a receptacle or cover that will accommodate separation of a syringe from a fully covered, used needle, after the needle has been covered by pushing it into the cover and away from the user's or operator's body and fingers.

Still another object is to provide a syringe and needle closed container that is useful also to safely receive the syringe and needle after use.

FEATURES OF THE INVENTION

Principal features of the invention include a body with a tubular needle receiving portion projecting from a cradle as the cover portion that will receive and secure the syringe of a hypodermic needle. Projecting finger engaging shields are provided around a finger grasping section of the cradle, and the connection between the cradle and a barrel end is flared to accommodate insertion of the needle tip and telescoping of the syringe into that barrel. Detent means are preferably provided in the inlet to the barrel end for holding the needle during unthreading of the syringe from the needle with the tapered barrel grasping and frictionally holding the needle against withdrawal from the barrel.

Another embodiment of the invention provides a shield device to maintain the sterility and integrity of a syringe, with or without an attached needle, before use, and which also provides for safely reinserting the needle and syringe into the shield device after use. The design of the shield device is such that, on reinsertion of the needle into its holder, the needle will, at all times, be pointing and moving away from the user's or operator's hands, thus preventing accidental needle stick injury. Further in this embodiment, the used needle will be securely encased s as to prevent later injury to another healthcare worker.

Additional objects and features of the invention will become apparent from the following detailed description and claims.

THE DRAWINGS

DETAILED DESCRIPTION

Figure 1:
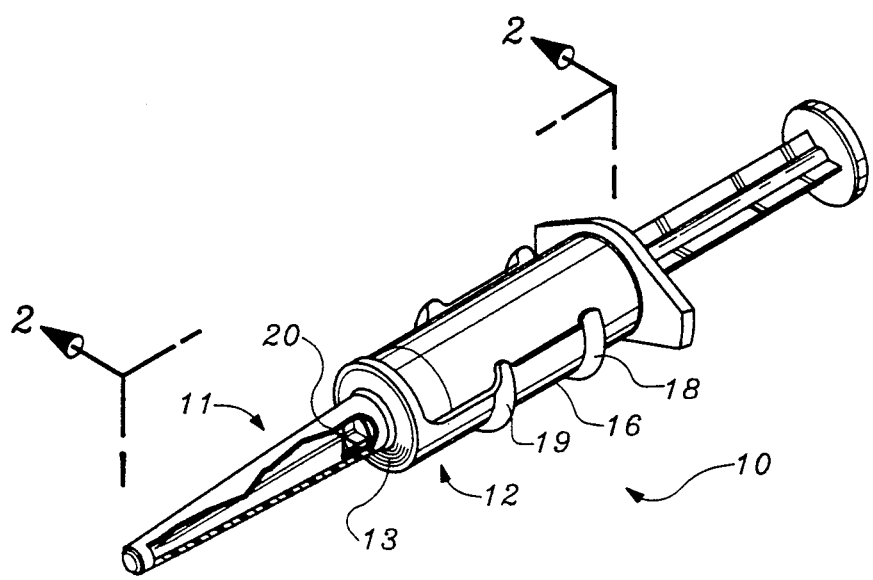
FIG. 1, is a perspective view of the needle receptacle of the invention.
Figure 2:
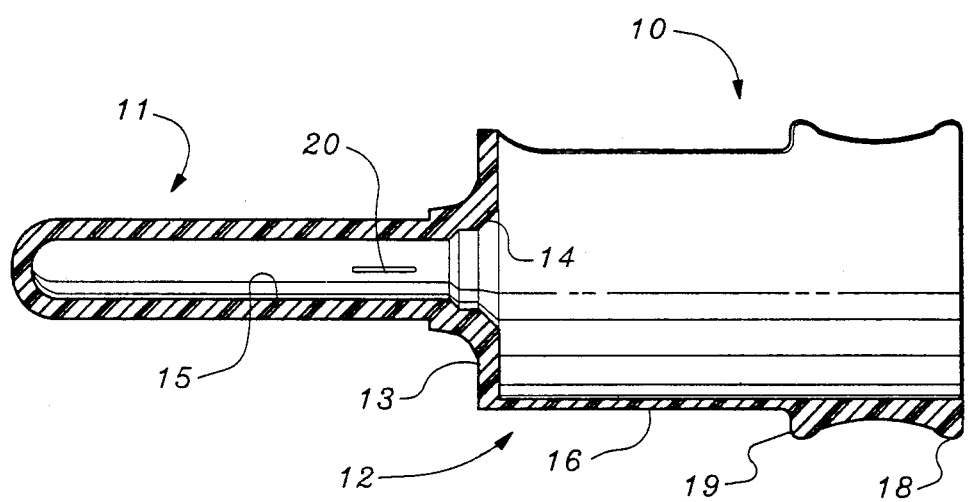
FIG. 2, is a longitudinal section, taken on the line 2—2 of FIG. 1.
Figure 3:
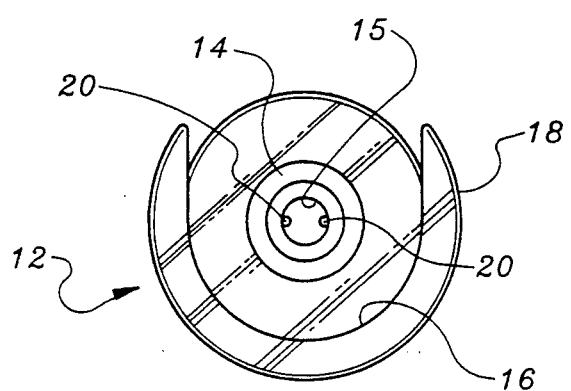
FIG. 3, is a rear elevation view.

Referring now to the drawings:

In the illustrated first preferred embodiment of FIGS. 1 through 3, the needle receptacle of the invention shown generally at 10, includes a needle receiving barrel portion 11 and a cradle portion 12. The barrel portion extends from a forward wall 13 of the cradle portion and has a flared barrel opening 14 that funnels into a tapered barrel 15 that is closed at its opposite end. The cradle portion 12 is of generally cylindrical configuration with its sidewall 16 partially cut-away back from the forward wall 13 to accommodate a syringe fitted therein.

A pair of spaced apart rings 18 and 19 extend around and project outwardly from the sidewall 16, defining a space between which rings 18 and 19 that serve as a finger grasping portion for an operator. A detent 20 projects inwardly of the barrel receiving portion adjacent to the tapered barrel 15. The detent 20 is to fit between wings formed on an upper end of some hypodermic needles for holding such a needle against rotation as the attached syringe is screwed onto or off the needle. Barrel 15 is to fit snugly around such needle wings so as to hold the needle against being withdrawn as the syringe is removed.

In use, a user grasps the sidewall 16 between the rings 18 and 19 with their thumb and forefinger to position the cradle portion above the hand and with the barrel 15 pointing away from the user. The syringe, that is positioned in the needle receptacle 10, is then raised and the needle is pulled from the barrel 15. After the needle is used, the sidewall 16 is again held in the same manner and the needle is guided tip from above into the barrel into and through the tapered barrel opening 14 and the syringe is then pivoted to position it in the cradle. Thereafter, if desired, the syringe can be unscrewed from the needle while the needle is held against rotation by detent 20 and is frictionally held in the barrel.

Figure 4:
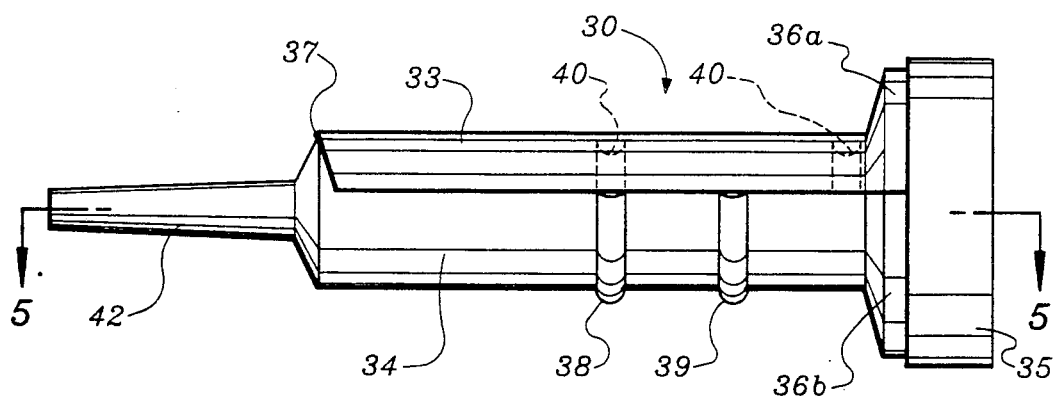
FIG. 4, is a side elevation view of a second embodiment of the invention in a needle and syringe cradle type housing having a removable end cap and upper portion to convert the housing into a receptacle.
Figure 5:
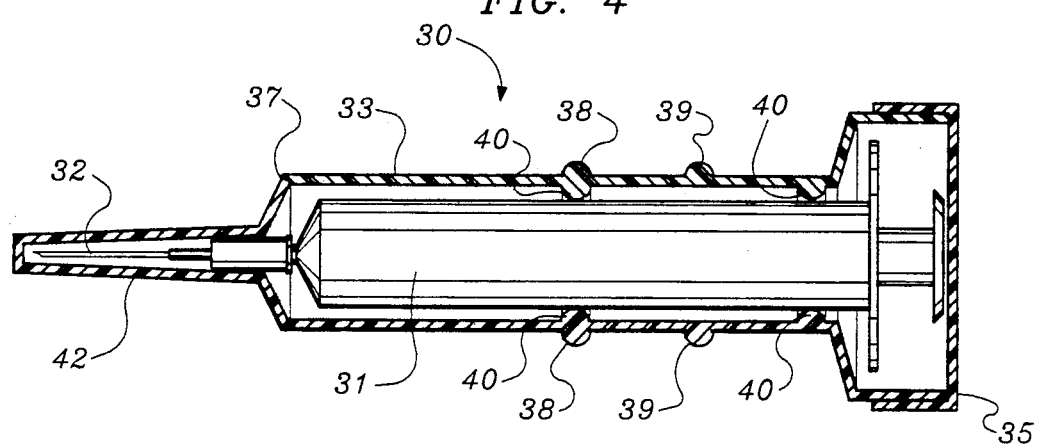
FIG. 5, is a top plan sectional view taken along lines 5—5 of FIG. 4.
Figure 6:
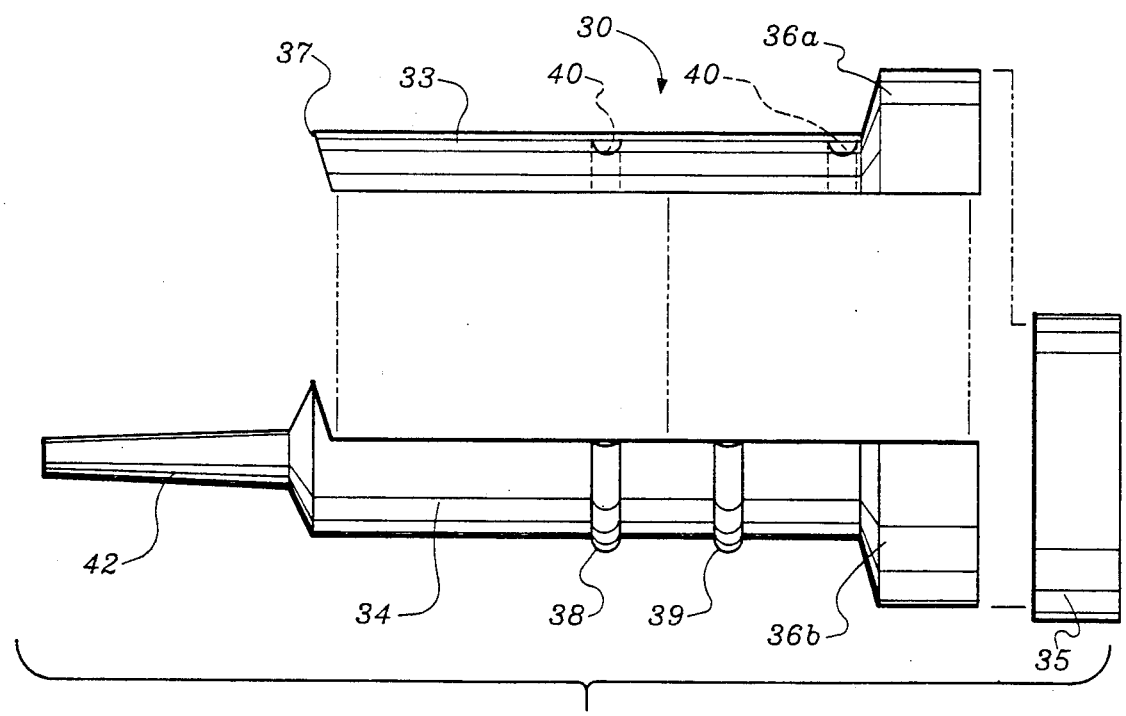
FIG. 6, is a side elevation view of the embodiment of FIG. 4, showing the end cap and upper portion of the protective housing exploded away.

FIG. 4 shows a complete housing 30 that is constructed to hold a syringe 31, shown in FIG. 5, either with or without an attached needle 32. Shown in FIG. 6, a top portion 33 fits to cradle portion 34 in such a way as to contain the syringe, preventing contamination. A cap consisting of an end piece 35 is to fit over the larger ends 36a and 36b, respectively, of the top portion 33 and cradle portion 34, capping the housing end. The end piece 35 that is held in place until use by plastic welds, or the like, not shown, that may be easily broken by a slight twist. To access a syringe contained within the housing 30, the end piece 35 is twisted off and the upper portion is bent upwardly breaking at a plastic weld 37, as shown best in FIG. 4. Both the end piece 35 and the upper portion 33 can then be discarded and the syringe 31 is removed for use, the needle 32 for injecting medicinals, or removing body fluids.

To reinstall the syringe 31 and needle 32 into the cradle portion 34 the operator grasps the cradle portion 34 that includes parallel spaced apart flange rings 38 and 39 for use as stabilizers. The syringe 31 is held in the operator's other hand, and is then lowered into the cradle portion 34 such that the needle 32 points and is moved away from the operator's hands. Elevated ribs 40 extend concentrically within the cradle portion and are to aid in the alignment of the syringe 31 so as to fit the needle into the cradle portion receiving barrel 42. Once the syringe is lowered into the cradle portion 34, it is pushed forward with the needle 32 entering the receiving barrel 42, wherein it is held in place by friction. Which receiving barrel 42 may include the detent 20 for use as described above with respect to needle receptacle 10. The used syringe and needle may then be discarded in an appropriate infectious waste receptacle. The used needle 32 will thereby remain encased in a receiving barrel 42 thus eliminating the possibility of its piercing such infectious waste receptacle.

Although preferred forms of our invention have been herein disclosed, it is to be understood that the present disclosure is by way of example and that variations are possible without departing from the subject matter coming within the scope of the following claims and a reasonable equivalency thereof, which subject matter we regard as our invention.

We claim:

1. A receptacle for a hypodermic needle comprising a rigid one-piece body having a cradle portion that is open along a top thereof to receive a syringe barrel of a hypodermic needle syringe; a tapered needle receiving closed end barrel portion extending from one end wall of said cradle portion to receive a needle of a hypodermic needle syringe; a flared barrel opening connection for receiving and guiding a syringe needle therethrough is arranged between said cradle portion and said tapered needle receiving closed end barrel portion; and said cradle portion includes a pair of spaced parallel upstanding partial rings with a finger or thumb receiving sidewall therebetween, transverse to the longitudinal axis.

2. A receptacle for a hypodermic needle as in claim 1, further including with the cradle portion a break-away top cover means for enclosing said cradle portion into a cylinder; said cradle portion end opposite to the needle receiving barrel portion end wall and the top cover means end are stepped outwardly to accommodate the hypodermic needle syringe plunger end; and a cap means arranged for covering over the cradle portion and top cover means stepped ends.

3. A cover for a hypodermic needle as in claim 2, wherein the cap means is spot welded to break when twisted off from the cradle portion and top cover means stepped ends.

4. A receptacle for a hypodermic needle as in claim 1, further including detent means projecting into the flared barrel opening connector to hold a needle inserted therein against rotation.

5. A receptacle for a hypodermic needle as in claim 1, further including spaced concentric elevated ribs projecting into the cradle portion to engage, support and guide a syringe installed therein.

6. A receptacle for a hypodermic needle comprising, a body having a cradle portion that is open along its top to receive and snugly support a syringe barrel of a hypodermic needle syringe; a pair of parallel upstanding partial rings formed transverse to said cradle portion longitudinal axis with a finger or thumb receiving closed end sidewall therebetween; and a needle receiving barrel portion projecting from an end of said cradle portion and having a tapered opening thereinto that connects said needle receiving closed end barrel portion interior and the interior of said cradle portion whereby a needle on the syringe is insertable through said cradle portion into the interior of said needle receiving closed end barrel portion as the syringe barrel is moved into said cradle portion.

* * * * *